United States Patent [19]

Kurland

[11] 4,400,833
[45] Aug. 30, 1983

[54] MEANS AND METHOD OF IMPLANTING BIOPROSTHETICS

[76] Inventor: Kenneth Z. Kurland, 2 W. McCabe Rd., El Centro, Calif. 92243

[21] Appl. No.: 272,134

[22] Filed: Jun. 10, 1981

[51] Int. Cl.³ .......................... A61F 1/00; A61F 1/24
[52] U.S. Cl. ................................................ 3/1; 3/1.4; 3/1.91; 3/1.911; 128/1 R; 128/334 R; 128/92 C
[58] Field of Search ............... 3/1, 1.4, 1.5, 1.9–1.913; 128/334 R, 334 C, 1 R, 92 C

[56] References Cited

U.S. PATENT DOCUMENTS

| 2,127,903 | 8/1938 | Bowen | 3/1.4 X |
| 3,176,316 | 4/1965 | Bodell | 3/1 |
| 3,514,791 | 6/1970 | Sparks | 3/1 |
| 3,577,837 | 5/1971 | Bader, Jr. | 128/334 R X |
| 3,842,831 | 10/1974 | Beisang et al. | 128/334 R X |
| 3,879,767 | 4/1975 | Stubstad | 3/1.91 |
| 3,894,530 | 7/1975 | Dardik et al. | 3/1 X |
| 3,938,528 | 2/1976 | Bucalo | 3/1 X |
| 3,973,277 | 8/1976 | Semple et al. | 3/1 |
| 3,974,526 | 8/1976 | Dardik et al. | 128/334 R X |
| 4,156,296 | 5/1979 | Johnson et al. | 128/92 C X |
| 4,187,558 | 2/1980 | Dahlen et al. | 3/1 |
| 4,201,216 | 5/1980 | Mattei | 3/1 X |
| 4,218,782 | 8/1980 | Rygg | 3/1.5 |

FOREIGN PATENT DOCUMENTS 2004465  4/1979  United Kingdom ................. 3/1.911

OTHER PUBLICATIONS

"Use of Cutis as an Interposing Membrane in Arthroplasty of the Knee", by J. E. Brown et al., The Journal of Bone & Joint Surgery, vol. 40-A, No. 5, Oct. 1958, pp. 1003-1018.

Primary Examiner—Ronald L. Frinks
Attorney, Agent, or Firm—Charmasson & Holz

[57] ABSTRACT

A means and method for implanting bioprosthetic material surgically, in humans or animals, is disclosed. The means comprise lengths of connective tissue such as cow tendons which are covered entirely or partially with a synthetic, looseweave mesh which is stitched to the tendon and which augments the strength of the finished heterograph (or xenograph) by permitting the existing live tissue to grow around the mesh to provide a living bond. Another implementation of the basic idea involves the use of planar patch material such as porcine pericardium to which the mesh is bonded on one side, or part of one side, this patch being used in various ways, for example, hernia repairs, dural patches, arthroplasties, tendon pulleys, gliding surfaces, and blood vessel anastamoses.

8 Claims, 24 Drawing Figures

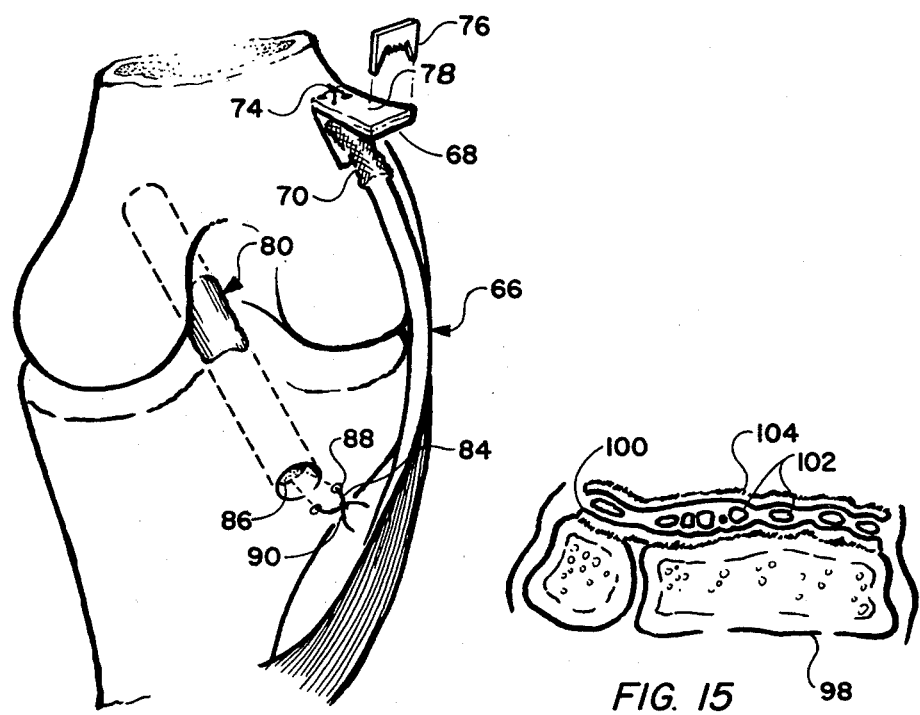
FIG. 11
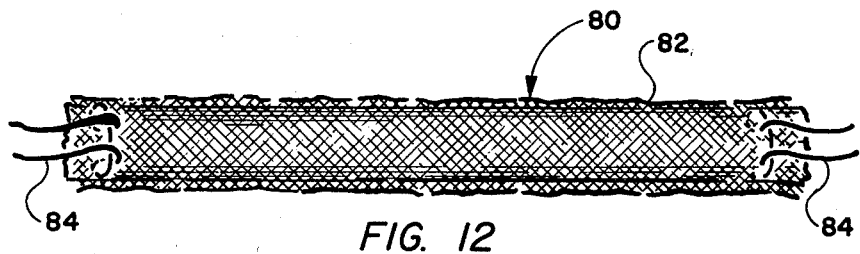
FIG. 12
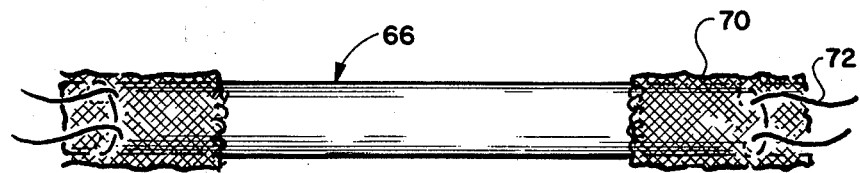
FIG. 13
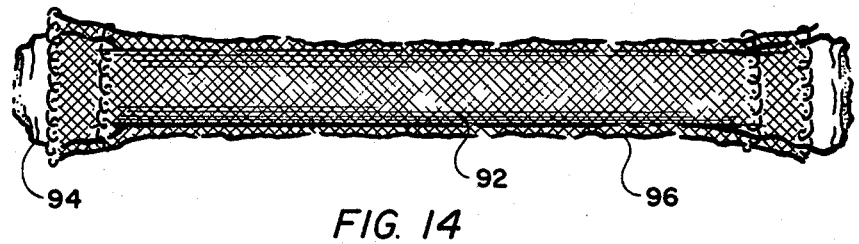
FIG. 14
FIG. 15

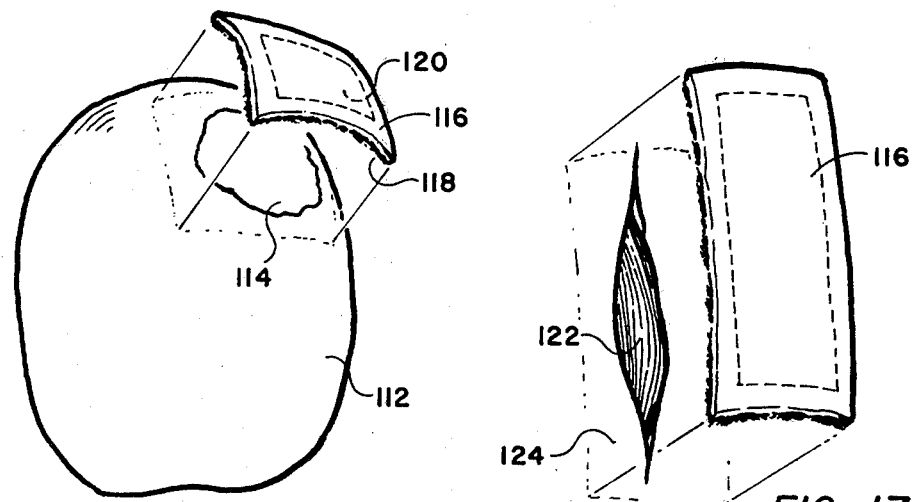
FIG. 16
FIG. 17
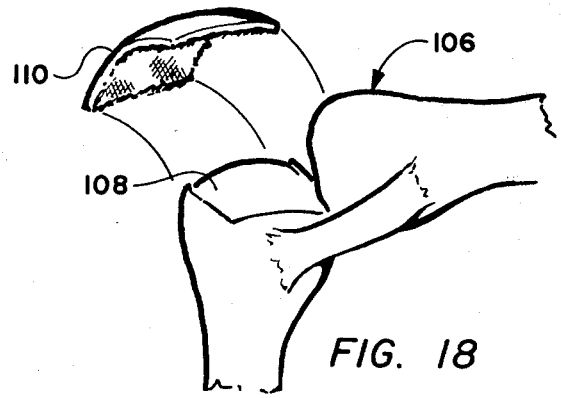
FIG. 18
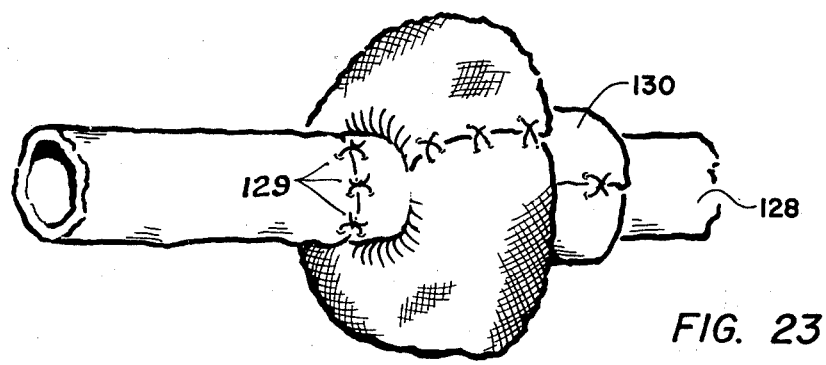
FIG. 23
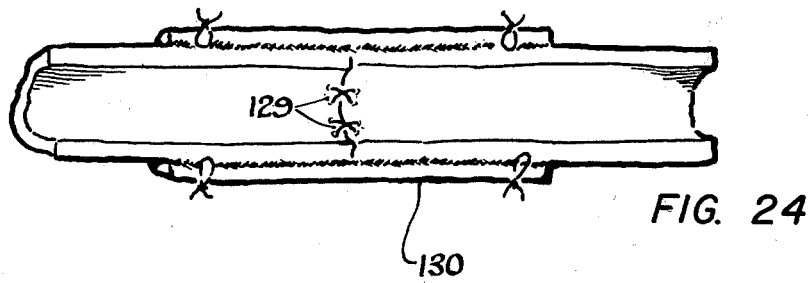
FIG. 24

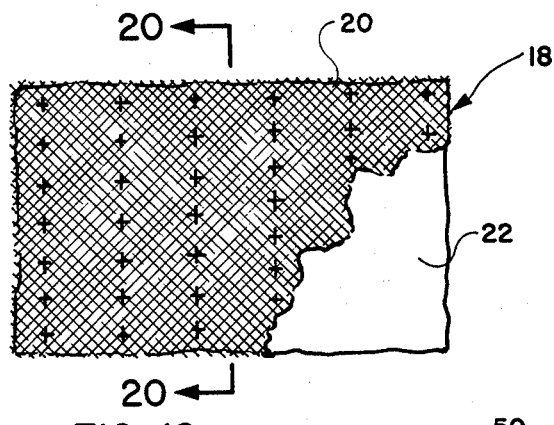
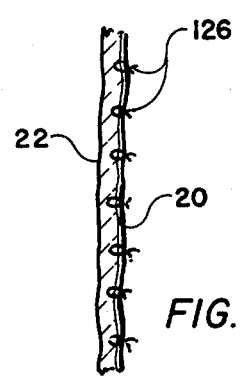
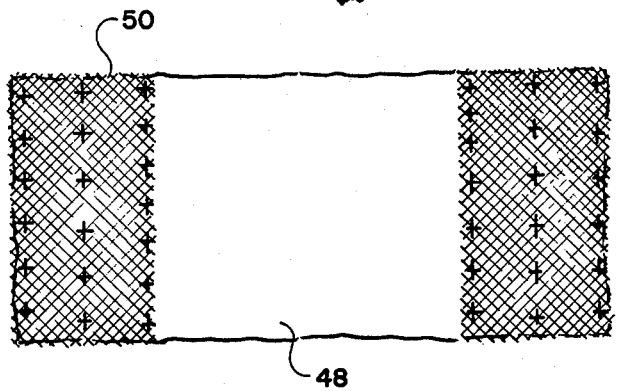
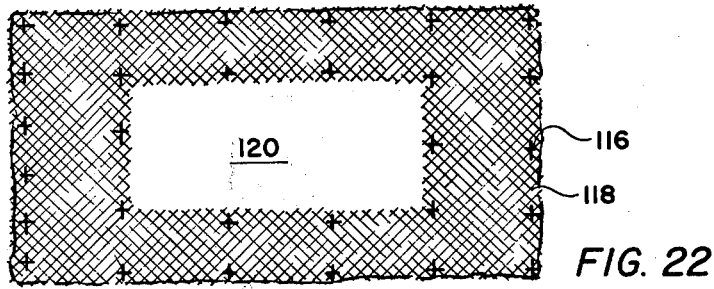

MEANS AND METHOD OF IMPLANTING BIOPROSTHETICS

BACKGROUND OF THE INVENTION

The invention is in the field of prosthetics and more particularly bioprosthetics, pertaining specifically to repair and replacement of connective tissue structures through use of heterologous animal tissue covered in whole or in part by a grid or mesh of synthetic fabric which is bonded to the heterologous tissue to provide the opportunity for host tissue ingrowth to define a living bond between the host tissue and the heterograft (or xenograft.) This method would also be applicable to homologous tissue.

The use of prosthetic devices within the body, such as artificial joints and plastic or metal implants of various kinds is becoming increasingly common and represents a technical field of intense activity. The use of biologically inorganic materials, such as metal or plastics, in the body creates basic engineering or mechanical problems, some of which can be overcome by the use of bioprosthetic material.

There are materials which are produced by the human body or in animals which are intrinsically superior to man-made materials in their durability, toughness, slipperyness, or a certain combination of desired traits. For example, it has been found that heart valve replacement can be done using porcine heart valves. Although mechanical valves have been developed, the porcine heart valve combines the characteristics of durability, reliability, and relative silence in operation and is inclined in the spectrum of today's prosthetic valve replacements. Porcine pericardium has also been used both to repair injured human pericardium and, at least once, to replace a single cusp in a defective heart valve.

Until recently, because of the antigenic nature of non-autologous tissue utilization of porcine heart valves and other bioprosthetic material had not been possible due to rejection. Currently, however, heterologous and homologous tissue may be rendered stable and non-antigenic by fixation with such compounds as glutaraldehyde to permit their use as heterografts in humans.

As pointed out below, the ability to use heterogeous animal tissue possessing similar biomechanical properties as those tissues being replaced or augmented has certain advantages, such as similar modulus of elasticity and the potential for eventual biologic bonding.

SUMMARY OF THE INVENTION

The instant invention takes advantage of the development of the glutaraldehyde fixation technique and basically utilizes stock heterologous animal tissue combined with synthetic mesh as body building materials.

Although the tissue used is often referred to in this specification and claims as heterologous, it will be understood that in all instances this term will be read broadly enough to cover homologous tissue from human cadavers.

In one main embodiment, the heterologous animal tissue comprises tendons or ligaments from cows or other animals which are used to replace human tendons or ligaments. After being fixed, the tendons or ligaments are covered all or in part, depending on which surfaces need to slide and which need to be gripped by surrounding tissue, by the synthetic mesh, which would ordinarily be stitched into place. In the event of a tendon or ligament-to-bone junction, the mesh-covered end of the heterologous tissue would be drawn into a bore or notched opening in the bone, where it is secured by sutures or other fixation. The presence of the mesh on the end of the bioprosthesis permits ingrowth of connective tissue to define a living bond with the bioprosthetic implant.

Other embodiments revolve around the use of a flat tissue such as the pericardium of pigs, which is prepared on one side, or part of one side, by the bonding of synthetic mesh thereto. The resulting product can be used in a number of applications, the basis of its use lying in the fact that those areas of the pericardium or other heterologeous patching tissue which need to bond to host tissue are covered with synthetic mesh to encourage host tissue ingrowth and tighter bonding, whereas those areas of the patch winch will be in contact with organs, or covering defects, or will act as sliding or bearing surfaces for moving body parts, will be left free of the mesh so that the naturally smooth, slippery pericardial tissue surface is utilized.

BRIEF DESCRIPTION OF THE DRAWINGS

FIG. 11 illustrates two types of ligament heterografts;

FIG. 12 illustrates a pre-wrapped heterograft specimen;

FIG. 13 represents a heterograft specimen as that of FIG. 12 but with mesh surrounding the tips only;

FIG. 14 is a side elevation view of a heterograft utilizing an animal ligament which is removed from the animal complete with bone fragments at the end;

FIG. 15 is a section through a hand indicating the use of the pericardium laminate as a sliding surface over the hand bones and to prevent the formation of scar tissue connecting tendon repairs to the bones;

FIG. 16 diagrammatically illustrates a dural patch;

FIG. 17 is a perspective of a repair of a defect such as in a flat muscle;

FIG. 18 illustrates utilization of the pericardium laminate in joint anthroplasties;

FIG. 19 is a front elevation with a portion cut away of a typical pericardium laminate;

FIG. 20 is a section taken through line 20—20 of FIG. 19;

FIG. 21 is a front elevation view of the pericardium laminate with a variant mesh pattern;

FIG. 22 is a view similar to 21 with yet another variant of the mesh pattern;

FIG. 23 illustrates utilization of the laminate in blood vessel anastomosis, or bioprosthetic graft to a blood vessel anastomosis;

FIG. 24 is a sectional view of a completed blood vessel anastomosis.

DETAILED DESCRIPTION OF THE PREFERRED EMBODIMENT

Figure 1:
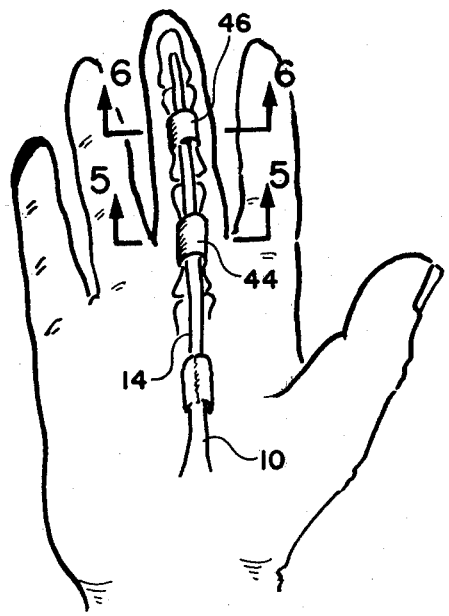
FIG. 1 diagrammatically illustrates the replacement of a finger tendon with a bioprosthetic tendon.

Uses of the instant technicque include applications in humans or other species utilizing heterologous ligmanets as replacement for or augmentation of previously existing ligaments, and reconstruction of tendons about the extremities, such as the wrist, hand, or lower extremities. Reconstruction of a finger and hand tendon is shown in FIG. 1, wherein the existing tendon is shown at 10. The existing tendon, which originally connected to the end of the middle finger, now terminates at the new juncture 12, at which point an artificial tendon 14 is connected. The artificial tendon is a specimen of connective tissue such as a tendon or ligament, from a cow or other animal which has been treated with glutaraldehyde or the like to render it nonantigenic and stable.

The connective tissue that is claimed is "regular" connective tissue, which is defined to mean tendons or ligaments, which have dence, closely packed collagenous connective tissue with the fibers arranged in parallel bundles with frequent interconnections, as opposed to other types of connective tissues such as scar tissue which has randomly oriented collagenous fibers, and umbilical cord tissue which is a loose, mucus connective tissue of low tensile strength.

Figure 3:
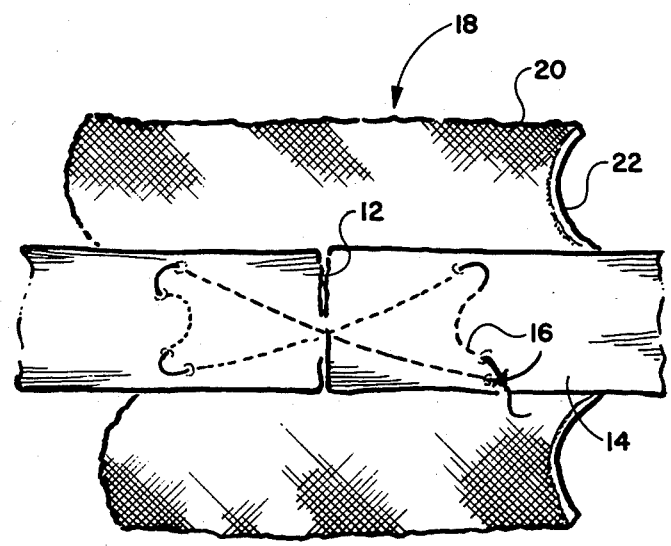
FIG. 3 illustrates the juncture between host and heterologous connective tissue before binding with the pericardium patch.

The artificial tendon, being actual mammalian connective tissue, may function quite adequately as a finger tendon, but needs to be anastamosed to the distal phalanx of the finger and to the proximal tendon stump 10. To connect to the existing tendon, as shown in FIG. 3, a suture 16 can be used to join the two ends. The Figure makes the point that the two ends are sutured together and does not necessarily indicate the optimal suturing technique.

In order to both strengthen and smooth over the juncture between the two tendon ends, and to encourage the ingrowth of tissue from the existing tendon 10, the juncture 12 is wrapped with a layer of mesh-backed pericardium 18, with the mesh 20 being on the inside, and the pericardium 22 being outside. It is an apparent characteristic of the pericardium that it will provide a very effective, smooth gliding surface to which live tissue will not grow, so that scar tissue forming around the injured area will not adhere to the tendon and prevent its subsequent gliding.

Figure 4:
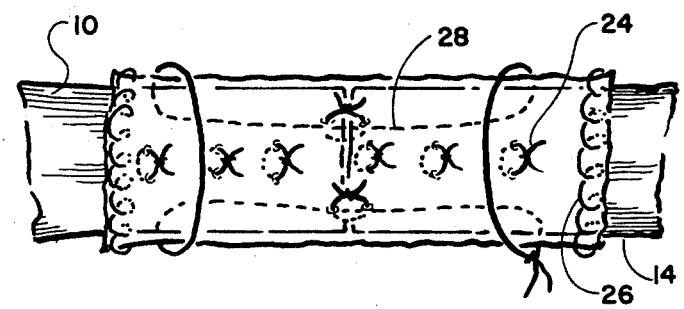
FIG. 4 represents the juncture of FIG. 3 after binding with the percardium sleeve.

The laminate is wrapped around the juncture as shown in FIG. 4, and can then be stitched to the respective tendon and artificial tendon with trough stitches 24, which pass through the connective tissue, and loop stitching 26 to fasten down the end edges. An additional FIG. 8 stitch 28 could be included to add extra strength.

As indicated above, the resulting connection will have a smooth exterior surface because of the external surface of the pericardium, and will also may exhibit strength that is greater than the straight end-to-end stitch which would otherwise be used.

Figure 2:
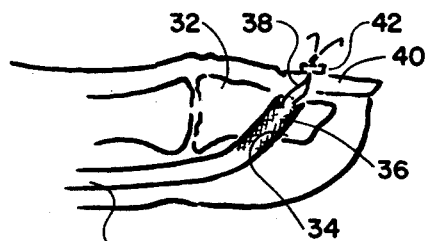
FIG. 2 is a sectional detail illustrating the connection of the heterograft to the fingerbone.

Turning to the other end of the artificial tendon 14, FIG. 2 illustrates a finger bone 32 through which has been drilled a tunnel 34. The distal end of the artificial tendon 14 is covered with a mesh cap or sleeve 36, which is sutured to the underlying artificial tendon as will be detailed below. The mesh, much as the mesh 20 stitched to the pericardium in FIGS. 3 and 4, permits the ingrowth of surrounding tissue. This mesh tip is pulled through the tunnel 34 and maintained in place by sutures 38 which extend through the nail 40 and are tied around a button 42. These sutures may be made as a part of a manufactured bioprosthetic tendon, or they can be added at the time of the operation. They remain in place long enough for the bone and/or connective tissue to adhere to the artificial tendon 14, which is greatly strengthened by the ingrowth of the bone tissue into the gridwork of the mesh cap 36. Either the sutures 38 are absorbable or they may be removed once connective tissue into the end of the bioprothesis is sufficiently strong.

Thus it can be seen that the combination of heterologous animal tissue with a mesh cover can be effectively used both to strengthen a graft and to permit tissue ingrowth, and thus foster live tissue bonding. An additional use of the general concept of heterologous tissue backed by mesh can be seen in FIGS. 1, 5 and 6 wherein the final structural members required to complete the construction of the finger tendon shown in FIG. 1 are detailed. These are the pulleys 44 in FIG. 5 and pulley 46 detailed in FIG. 6, which exists in a natural human hand and prevent bow-stringing of the tendon as the finger is flexed. Although there is no reason pulleys 44 and 46 should differ from one another, they are shown different to illustrate two embodiments. Pulley 44 utilizes a strip of pericardium 48 with mesh bands 50 across the ends of one side. With the mesh side in, the pulley is stitched to the periostium of the phalanx 52, where in a manner similar to that detailed with reference to FIG. 2, connective tissue ingrowth around the mesh 50 will create a strong bond over a period of time. The mesh terminates well short of the artificial tendon 24 so that the smooth pericardium surface provides a slick bearing surface for the longitudinal motion which the tendon requires. FIG. 6 illustrates an arrangement that is identical to FIG. 5 except that the ends of the heterograft overlap and are stitched together in their overlapping ends. They would be stitched to the periostium as well to prevent migration and to foster connective tissue ingrowth as was the case in FIG. 5.

Thus the sequence of procedure shown in FIGS. 1 through 6, used to reconstruct a hand tendon, provide a basic, coherent illustration of all of the techniques and materials used in the instant procedures. Tendon anastomosis illustrated in FIGS. 3 and 4 utilizes the laminate or patch 18 to provide a strengthening, smooth sleeve across the point of anastomosis. At the other end, the heterologous tendon with the synthetic mesh sleeve is pulled into a bone tunnel, illustrating a bioprosthesis-to-bone connection. Intermediate the two ends, the utilization of the pericardium for low-friction sliding purposes is illustrated. The product used in this instance is similar to the laminate 18, but of course does not have a continuous cover of mesh, but only two bands of mesh across either end of one side.

Figure 7:
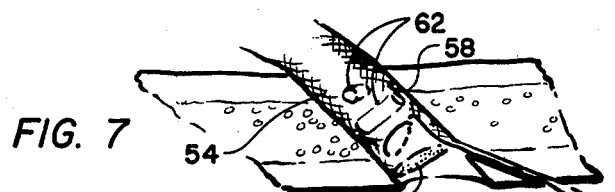
FIG. 7 is a section through a bored bone showing a slightly modified technique of connecting bone to connective tissue.
Figure 8:
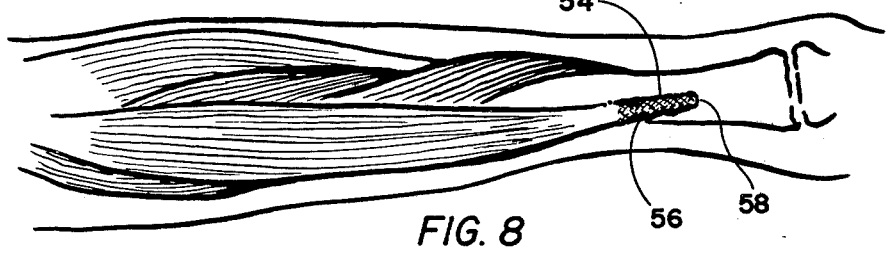
FIG. 8 is an elevation view of the musculature and bone structure utilizing the connective technique of FIG. 7.

FIGS. 7 and 8 illustrate a procedure similar to that shown in FIG. 2, but on an arm. In this instance, the end of a real or artificial tendon 54 is covered with a mesh sleeve 56 and inserted part way through a bone tunnel 58. To maintain the end in place pending healing, sutures 60 are pulled through a pair of small holes drilled in the bone adjacent the main tunnel 58. A pair of transverse bone plugs 62 have been inserted through the ends of the tendon for the purpose of contacting the bone alongside the bone tunnel 58, so that it will fuse together over time. The bone plugs may be inserted into incisions made in the ends of the tendon when the operation is taking place. The bone fragments used for the plugs may be obtained from local or areas of the recipient's skeletal structure, or may be homologous or heterologous. Additionally, a similar result could be achieved by passing absorbable sutures through the ends of the bioprosthetic. As these stitches slowly dissolve, they will leave passageways for the ingrowth of surrounding tissue. This technique may be used with other forms of the bioprosthetic showing herein as well or the tendon and ligament grafts.

Figure 9:
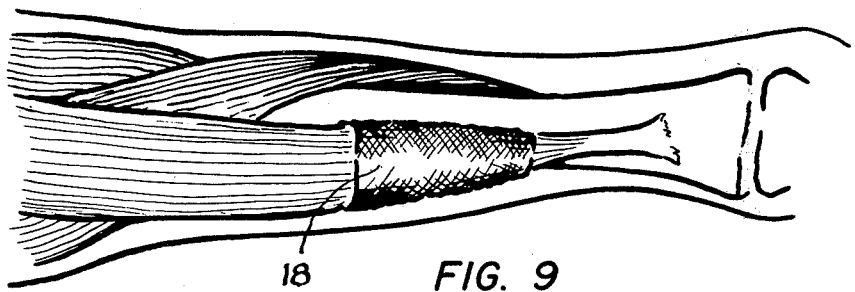
FIG. 9 illustrates a simple tendon repair utilizing pericardium laminate, or the protective sheathing of a muscle or tendon.
Figure 10:
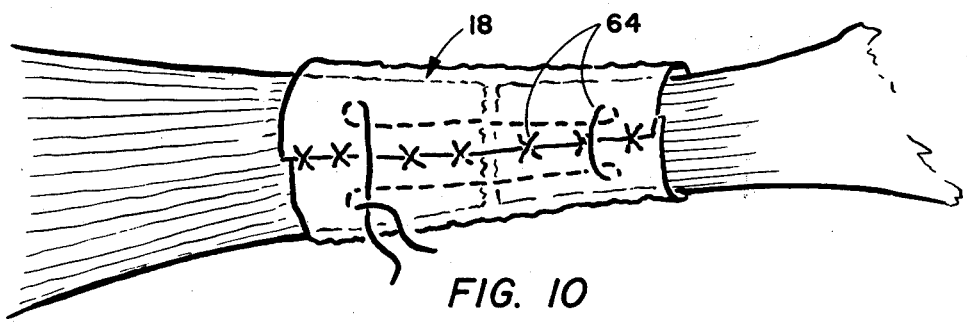
FIG. 10 is a detail of the repair shown in FIG. 9.

FIGS. 9 and 10 illustrate a simple tendon anastomosis utilizing the laminate 18 in the same fashion as illustrated in FIGS. 3 and 4. In this instance, there is no need for an artificial tendon as both ends of the original tendon are present. Once the two ends are sutured, the sleeve is wrapped around and connected to itself and to the underlying tendons with sutures. Tendon adherance to the mesh is again desired, and the external pricardium surface will again provide a smooth, non-bonding surface to permit some motion of surrounding tissue across the pericardial surface and prevent scar tissue adherance. FIG. 9 can also illustrate the sheathing of an existing unbroken muscle with the laminate to reduce friction at a sore or injured point. The same could be done to a peripheral nerve with the laminate bioprosthetic sutured to the epineurium to prevent abrasion, chaffing or tissue ingrowth from surrounding tissue.

In FIG. 11 a knee joint is shown having two artificial ligament grafts illustrating two variant means of connection of the ligament ends to the bone structure. The collateral ligament 66 connects to the bone on opposite sides of the joint in windows 68 cut into the bone with an osteotome. This ligament is shown in more detail in FIG. 13. The body of the ligament replacement, that is the tissue itself, would ordinarily be a tendon or ligament from a cow or other animal. At each end a mesh cap or sleeve 70 is securely stitched to the tendon or ligament tissue. A suture 72 extends from each end, and as can be seen from FIG. 11 these sutures are drawn through the bone and tied as indicated at 74 to initially hold the ligament in place. Additional strength can be achieved by utilization of a staple 76 which drives straight through the bone flap 78 which was cut by the osteotome and into the metaphysis.

Over a period of time, the windows 68, of course, fill in with bone, and in doing so grow interstitially among the fibers of the mesh caps 70 so that a permanent, strong and secure artificial ligament connection is effected.

Turning to the other ligament in FIG. 11, this is a cruciate ligament replacement, and the replacement element is indicated at 80 and is detailed in FIG. 12. Here again, a bovine tendon or ligament would ordinarily be used. Because there is no sliding or slipping of the ligament across another surface, the entire length of the graft can be covered with the mesh 82, which, again, is securely stitched to the underlying tissue. Sutures 84 extend from the ends of the heterograft.

When installed in the bone as shown in FIG. 11, a continuous tunnel 86 is formed with a surgical drill, and the artificial ligament 80 is extended through this bore with the sutures 84 being drawn through small suture holes 88 and tied at 90. Again, over time bone ingrowth should essentially fill all interior space. To expedite this ingrowth process, as a matter of surgical technique often bone powder and chips from the drilling, which form a kind of paste, are inserted in the ends of the bore 86 to implement formation of a contiguous bone mass.

The heterografts shown in FIGS. 12 and 13 are exemplary of off-the-shelf items which would be provided in different shapes and sizes by surgical companies and selected from an array of different types for use by the surgeon. Although created in large part from actual animal tissue, they are made into produced and sold as such. A similar product 92 is indicated in FIG. 14. This item, also representing an artificial ligament, is an actual ligament from an animal, but in this instance the ligament is removed from the donor bone along with its bony attachments 94. Use of this specimen might require development of further techniques for rendering the bone tissue non-antigenic. This ligament would need to be removed along with its bony attachments so that these bone fragments are incorporated as an integral, organic part of the entire structure. Subsequently, the collagen portion of the ligament is wrapped with the mesh as indicated at 96 which is securely sutured in place.

Turning from the implementation of the invention as connective tissue, structural replacement or augmentation, FIGS. 15 and 18 illustrate use of the basic laminate 18 to define sliding or slippery bearing surfaces. In FIG. 15, a cross section of a hand is shown wherein the wrist bones 98 are covered with a segment 100 of the pericardium-mesh laminate with the mesh down so that it will bond to the bone and/or periosteum. The top surface of the laminate is the pericardium, and just above this surface are the tendons 102 of the hand, which are beneath the skin 104. By the utilization of the pericardium laminate between the bone and the tendons, not only is a smooth surface defined which may eliminate problems with roughness occuring in the underlying bone, but, more importantly, the growth of scar tissue around any tendon repairs above the bioprosthetic pericardium will not bond to the pericardium as it would to the underlying bone and soft tissue, and thus will not limit the motion of the hand as would otherwise be a problem in hand reconstruction. This implementation is similar in principle to that involving the pulleys 44 and 46 indicated in FIGS. 5 and 6. In both instances, the mesh is used to form a firm tissue bond, and the pericardium itself is used to define a sliding surface.

Another sliding surface is defined in FIG. 18 wherein an arthroplasty is performed on a joint 106. The joint may have become roughened or weakened with use, and a portion is removed to define a relieved area 108 which is capped with a section 110 of the laminate, of course with the face down to bond to the underlying bone. In this instance, the upper surface of the laminate which to this point has been described as pericardium, could possibly be cartilage instead of pericardium. In either instance, a smooth bearing surface is provided which was otherwise lacking in that particular surface of the joint.

In yet another general implementation of the technique, FIGS. 16 and 17 illustrate "patching" of defective planar tissue in the body by use of the pericardium and mesh structure. In FIG. 16, the dura 112 has a defect 114, which may result from a head injury or surgical intervention. Merely suturing the edges of the parted dura around the hole together is not adequate to cover the opening. Therefore, a patch 116 is utilized having a peripheral strip 118 of the mesh around the inner surface to bond to the dura alongside, but not covering, the opening 114. The patch is sutured into place, and over time the dura forms a stronger bond to the mesh trim 118, and the central, smooth portion 120 of the patch overlies the brain.

A similar configuration is shown in FIG. 17 wherein a patch 116 is numbered identically. In this instance, an elongated fascial defect 122 of the muscle tissue 124 requires repair. This situation may also be present in hernias, wherein the nature of the defect precludes suturing existing tissue together sufficiently to provide a satisfactory repair.

FIGS. 19 through 22 detail to some extent the product used in the patching implementations of the invention discussed above. The patch of FIGS. 16 and 17 is illustrated in FIG. 22, and the similar numbers are retained. Naturally, the shape of the patch need not be square and would ordinarily be trimmed by the surgeon in use. A variety of different sizes, shapes, and relative proportions of mesh versus unobstructed smooth space 120 would need to be provided if the item is to be used off the shelf, or substantially off the shelf, with some modification.

The basic laminate 18 is shown in FIG. 19, having a pericardium face 22 with the mesh backing 20. Ordinarily, the mesh would be connected to the pericardium with suitable sutures 126 so that the pericardium surface is not penetrated or marred.

Figure 5:
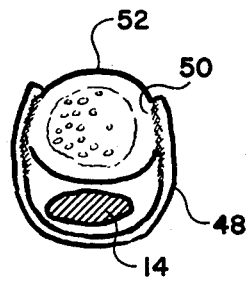
FIG. 5 is a section through line 5—5 of FIG. 1 illustrating one means of pulley installation.
Figure 6:
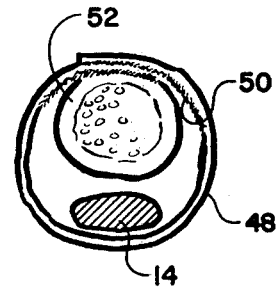
FIG. 6 is a section taken through line 6—6 of FIG. 1 representing annother means of pulley creation.

FIG. 21 is an enlargement of the configuration used in FIGS. 5 and 6 for the pulley construction. Clearly other geometric arrangements of the basic structure would be required for different specialized uses, although a basic variety of sizes and shapes and configurations might easily be adapted by cutting and trimming at the operation site to achieve the precise heterograft desired.

One further use of the laminate is shown in FIGS. 23 and 24. In this instance, a rectangular patch is used in a manner very similar to that indicated in FIGS. 3 and 4. However, instead of joining tendons, blood vessels 127 and 128 are connected, first with direct sutures 129 between the blood vessel ends proper, and secondly with the laminate sleeve 130. The sleeve may be sutured to one blood vessel end as shown in FIG. 23 and rolled back, subsequent to which the blood vessels are joined. Once the direct suturing between the blood vessels is finished, the sleeve 130 can be rolled flat as shown in FIG. 24, and sutured to the second blood vessel as shown.

Vessel 128 could also be a bioprosthetic blood vessel. In this instance, it could be provided off the shelf with the sleeve already fastened in place, and possibly rolled back as shown in FIG. 23.

Thus it can be seen that a basic concept, involving the bonding together of a synthetic mesh with heterologeous tissue, to make a heterograft, naturally expands into a variety of different applications requiring modified heterograft products. The mesh itself could be made of Dacron or any other suitable synthetic material woven or otherwise fabricated to meet specific requirements, and the heterologous tissue could be other than porcine. Undoubtedly other applications will become apparent as the invention is implemented. Falling within the generalized disclosure and the claims appended hereto, a product is provided comprising bioprosthetic material bonded to synthetic mesh, surgically implanted in such manner as to foster or promote host tissue ingrowth and subsequent fixation of the bioprosthesis.

While I have described the preferred embodiment of the invention, other embodiments may be devised and different uses may be achieved without departing from the spirit and scope of the appended claims.

What is claimed is:

1. A method of implanting bioprosthetic material in the body utilizing a length of regular connective tissue having a mesh bonded to at least one end thereof, said method comprising the following steps:
    (a) inserting said one end into a tunnel bored into a bone with the mesh in substantial contact with the living bone tissue; and
    (b) fastening said tissue specimen in place to permit growth of live tissue into said mesh and then into said length of regular connective tissue to define a living bond.

2. A method according to claim 1 and including the step of inserting at least one bone plug into said one end of said length of regular connective tissue and bringing said bone plug into contact with the sides of said tunnel during step (a) so that fusion of bone between said plug, tunnel walls, and length of regular connective tissue will eventually occur.

3. A modified bioprosthesis comprising:
    (a) a length of connective tissue still connected at at least one end to the bony attachment from the donor; and
    (b) a mesh bonded to at least one portion of the surface of said connective tissue such that said modified bioprosthesis can be placed with at least a portion of said mesh against a living tissue surface and held in place, and said living tissue will grow into said mesh to define a living bond therewith.

4. Structure according to claim 3 wherein said mesh substantially surrounds said connective tissue.

5. Structure according to claim 4 wherein said specimen comprises a cow tendon.

6. A bioprosthesis comprising:
    (a) a tissue specimen in the form of a length of regular connective tissue treated to be non-antigenic;
    (b) said length having at least one end designated for attachment to a bone of a patient to repair connective tissue damage; and
    (c) a synthetic mesh fastened to said one end and positioned thereon to interface between the length of connective tissue and the bone, whereby bone will grow around said mesh and into said one end of connective tissue to completely integrate said prosthesis into the physiology of the patient.

7. Structure according to claim 6 wherein said tissue specimen comprises a length of connective tissue substantially completely encapsulated in a mesh cover.

8. Structure according to claim 6 wherein said tissue specimen comprises a length of connective tissue having the ends thereof wrapped with mesh caps.

* * * * *

UNITED STATES PATENT OFFICE
CERTIFICATE OF CORRECTION

PATENT NO. : 4,400,833

DATED : August 30, 1983

INVENTOR(S) : KENNETH Z. KURLAND

It is certified that error appears in the above–identified patent and that said Letters Patent are hereby corrected as shown below:

In Claim 5 replace "specimen" with --connective tissue--.

Signed and Sealed this

Seventeenth Day of July 1984

[SEAL]

Attest:

GERALD J. MOSSINGHOFF

Attesting Officer

Commissioner of Patents and Trademarks